United States Patent [19]
Wand et al.

[11] Patent Number: 5,457,235
[45] Date of Patent: Oct. 10, 1995

[54] HALOGENATED DIPHENYLDIACETYLENE LIQUID CRYSTALS

[75] Inventors: Michael D. Wand, Boulder, Colo.; Sean D. Monahan, Madison, Wis.; William N. Thurmes, Longmont; Kundalika M. More, Denver, both of Colo.

[73] Assignee: Displaytech, Inc., Boulder, Colo.

[21] Appl. No.: 3,019

[22] Filed: Jan. 11, 1993

Related U.S. Application Data

[63] Continuation-in-part of Ser. No. 667,668, Mar. 11, 1991, Pat. No. 5,178,791.
[51] Int. Cl.[6] .................. C07C 319/00; C07C 41/00; C07C 17/00; C09K 19/06
[52] U.S. Cl. ................ 568/65; 568/66; 568/645; 568/647; 568/661; 556/425; 556/426; 556/465; 570/128; 570/184; 252/299.6
[58] Field of Search ............... 252/299.6, 299.01, 252/299.5; 570/128, 184; 568/65, 66, 645, 647, 661; 556/425, 426, 465

[56] References Cited

U.S. PATENT DOCUMENTS 4,431,263  2/1984  Garito .................... 359/42 X
4,895,975  1/1990  Fujiwara .................. 560/83

FOREIGN PATENT DOCUMENTS 383621  2/1990  European Pat. Off. .
3901266  7/1990  Germany .

OTHER PUBLICATIONS

Reiffenrath, V. et al. (1989) Liquid Crystals 5: 159–170.
Chemical Abstracts 114(10) 82718z, 1991.
Chemical Abstract 101(4) 24111s, 1984.

Abstract of oral presentation of Michael Wand at the Fourteenth International Liquid Crystal Conference in Jun. 1992 at Pisa, Italy. It is believed that the abstract was made available to attendees of the meeting in Jun. 1992.

Primary Examiner—C. Harris
Attorney, Agent, or Firm—Greenlee and Winner

[57] ABSTRACT

The present invention provides liquid crystals that are diphenyldiacetylenes of the general formulas:

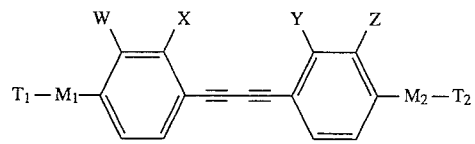

or

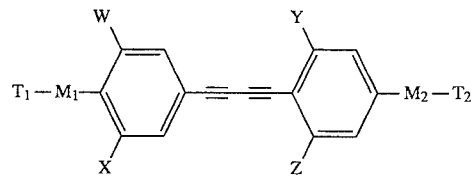

where W, X, Y and Z are, independently of one another, a halogen atom, a hydrogen atom or a trihalomethyl group, $T_1$ and $T_2$, independently of one another can be an alkyl, alkene, alkoxy, alkenoxy, ether, thioalkyl, thioalkenyl, haloalkyl, haloalkoxy or haloalkylether groups having from three to twenty carbon atoms or a silylalkyl, silylalkenyl, silylalkoxy or silylthioalkyl group having from three to twenty-eight carbon atoms and wherein $M_1$ and $M_2$ can both be single bonds or one of $M_1$ or $M_2$ can be a trans-1,4-cyclohexylene or a —$CH_2CH_2$-trans-1,4-cyclohexylene.

39 Claims, No Drawings

HALOGENATED DIPHENYLDIACETYLENE LIQUID CRYSTALS

This invention was made with partial support of the United States Government. The United States Government has certain rights in this invention.

This application is a Continuation-in-part of U.S. Ser. No. 667,668, filed Mar. 11, 1991, Pat. No. 5,178,79, issued Jan. 12, 1993, which is incorporated by reference herein in its entirety.

FIELD OF THE INVENTION

The present invention is in the field of liquid crystals useful in electro-optical and display device applications.

BACKGROUND OF THE INVENTION

Liquid crystals have found use in a variety of electro-optical and display device applications, in particular those which require compact, energy-efficient, voltage-controlled light valves such as watch and calculator displays. Liquid crystal displays have a number of unique characteristics, including low voltage and low power of operation, which make them perhaps the most promising candidate materials for non-emissive electro-optical displays available with current technology. Most of these devices are based upon the dielectric alignment effects in nematic, cholesteric and smectic phases of the liquid crystal compound in which, by virtue of dielectric anisotropy, the average molecular long axis of the liquid crystal molecules take up a preferred orientation in an applied electric field.

Twisted nematic (TN) liquid crystals are currently widely employed for display applications. TN devices and related super twist nematic (STN) devices require nematic liquid crystal compositions with positive dielectric anisotropy. Nematic LC device applications require chemically stable LC compounds or mixtures of compounds which display a nematic phase over a substantial temperature range, preferably about room temperature. Oftentimes, desired electrooptic properties can be achieved in a nematic liquid crystal by addition of dopants to nematic host materials. The kind and amount of such dopants added allows the tuning of electrooptic properties in the resultant mixtures. LC dopants which enhance or introduced desired electrooptic properties in LC mixtures without detriment to mesomorphic properties are important for the production of LC compositions for device applications. Nematic LC compositions having high birefringence are important for certain high contrast display applications. LC dopants which enhance birefringence in LC mixtures without detriment to mesomorphic properties are important for such high contrast applications.

In nematic-based display devices, the electro-optical response may be too slow for many potential applications. The requirement for fast response becomes especially important when the number of addressable elements in a device increases. Electro-optic effects with sub-microsecond switching speeds can be achieved using the technology of ferroelectric liquid crystals (FLCs) of N. A. Clark and S. T. Lagerwall (1980) Appl. Phys. Lett. 36:899 and U.S. Pat. No. 4,367,924. Display structures prepared using FLC materials can have high speed response (about 1,000 times faster than currently used twisted nematic devices) and also exhibit bistable, threshold sensitive switching. Such properties make FLC-based devices excellent candidates for light modulation devices including matrix-addressed light valves containing a large number of elements for passive displays of graphic and pictorial information, optical processing applications, as well as for high information content dichroic displays. A review of the applications of FLC devices is given by S. T. Lagerwall and N. A. Clark (1989) Ferroelectrics 94:3–62.

Tilted smectic liquid crystal phases, in particular smectic C phases, are useful in the preparation of FLC materials. Materials exhibiting such smectic phases which comprise chiral, nonracemic components possess a spontaneous ferroelectric polarization, or macroscopic dipole moment, deriving from a dissymmetry in the orientation of molecular dipoles in the liquid crystal phases (Myer et al. (1975) J. Phys. (Les Ulis, Fr) 36:L-69). The ferroelectric polarization density is an intrinsic property of the material making up the phase and has a magnitude and sign for a given material under a given set of conditions. In FLC devices appropriate application of an external electric field results in alignment of the molecules in the FLC phase with the applied field. When the sign of the applied field is reversed, realignment or switching of the FLC molecules occurs. This switching can be employed for light modulation. Within a wide range of electric field strengths, the switching speed (optical rise time) is inversely proportional to applied field strength and polarization or dipole density (P), and directly proportional to orientational viscosity. Faster switching speeds are thus associated with FLC phases which possess higher polarization density and lower orientational viscosity.

A basic requirement for application of ferroelectric liquid crystals in SSFLC devices is the availability of chemically stable LC compounds or mixtures which exhibit chiral tilted smectic phases, preferably chiral smectic C phases, over a substantial temperature range, preferably about room temperature. Some FLC-like devices require LC materials having a smectic A phase. In some cases, a chiral nonracemic LC material will possess an enantiotropic or monotropic chiral tilted smectic phase. FLC mixtures possessing chiral smectic phases, including those with smectic C* phases (i.e, chiral smectic C), with useful temperature ranges can also be obtained by admixture of chiral, nonracemic compounds, designated FLC dopants, into liquid crystal host material which exhibits a desired tilted smectic phase (an FLC host material) and which may or may not be composed of chiral molecules. Addition of the FLC dopant can affect the ferroelectric polarization density and/or the viscosity of the resultant FLC mixture and thereby affect switching speed. Desirable FLC dopants are molecules which impart high ferroelectric polarization density to an FLC mixture without significantly increasing the orientational viscosity of the mixture. Components of FLC mixtures can also be adjusted to vary phase transition temperatures or ranges.

Other properties of the FLC material, for example the tilt angle of the chiral smectic phase and the birefringence of the material, can affect their usefulness for particular device applications. These properties are affected by the structures of the various components and the amounts of these components in the FLC material. Most effort in the development of FLC materials has been directed toward flat panel display applications. The optimal characteristics for FLC materials used in such displays include high spontaneous polarization (Ps) and low orientational viscosity to achieve fast switching, tilt angles of 22.5° which result in maximum contrast in SSFLC cells switched between crossed polarizers, low birefringence which facilitates construction of a desirable thickness panel and broad temperature range (about room temperature). FLC materials useful in waveguides, integrated optics and spatial light modulators have somewhat different requirements. High polarization and low viscosity are desired for both display and optical switching FLC applications. Enhanced performance in optical switching FLC applications is correlated with high total refractive index change between the switched states which is associated with high birefringence and large tilt angles. A particular type of FLC display device, a dichroic display device containing color switching elements incorporating mixtures of FLCs with dichroic dyes, also requires high tilt FLC material to achieve highest contrast. (See Ozaki et al. (1985) Jpn. J. Appl. Phys. Part I 24 (Suppl. 24-3):63–65.) For applications requiring high tilt angle and/or high birefringence it is desirable to have FLC materials which combine these properties with fast switching speed and broad room temperature smectic C* phases.

Thermotropic liquid crystal molecules typically possess structures which combine a rigid core coupled with two relatively "floppy", i.e., structurally flexible, tails. The tails are typically coupled to the core such that the LC molecule can assume a configuration with relatively linear arrangement of the tails along the long axis of the core. (See Demus et al. (1974) Flussige Kristalle In Tabellen, VEB Deutscher Verlag fur Grundstoffindustrie, Lebzig.) A wide variety of nematic liquid crystal materials are known in the art. FLC materials have been prepared by introduction of a stereocenter into one or both of the tails of basic LC molecule structure, thus introducing chirality. A variety of FLC materials including materials having phenylbenzoate, biphenyl, phenylpyrimidine, phenylpyridine and tolane core structures have been reported. FLC host materials, having low polarization density or which are achiral, having such core structures have also been reported. FLC host materials typically possess smectic C phases. A number of chiral nonracemic FLC dopant materials are known in the art.

The present invention relates to halogenated and trihalomethyl-substituted diphenyldiacetylenes useful as components of nematic and ferroelectric LC compositions.

FLC compositions having tilt angles between 30° to 60° have been reported by Ichihashi et al. (1988) EPO publication No. 269,062. The authors infer that tilt angle in the smectic C phase depends on the ordering of liquid crystal phases exhibited by a material, in particular the absence of a higher temperature smectic A phase, is associated with high tilt in the smectic C phase. The reference provides the tilt angles of a number of smectic C phase LCs, no correlation between tilt angle and structure is disclosed. A related EPO application of Furukawa et al. (1988) Publication No. 220,747, refers to a method for controlling tilt angle in FLC smectic C mixtures. The method described involves controlling the tilt angle of a mixture by adjusting the composition of the mixture such that a smectic A phase is present (for low tilt mixtures) or absent (for high tilt mixtures). These references also refer to a number of components of LC mixtures some of which components have monofluorinated core moieties.

Diacetylenic liquid crystals have been reported by B. Grant (1978) Mol. Cryst. Liq. Cryst. 48:175–182 and E. M. Barrall et al. (1978) Liq. Cryst. Ordered Fluids 3:19–39. Symmetric 4,4'-substituted diphenyldiacetylenes having the general formula:

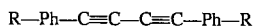

where R=n-alkyl or n-alkoxy were reported to have liquid crystal properties. The alkyl substituted derivatives were reported to exhibit only nematic liquid crystal phases. No smectic phases were reported with the alkyl derivatives. Most of the alkoxy derivatives similarly exhibited only nematic LC phases, however, the n-$C_{14}H_{29}O$ and n-$C_{15}H_{31}O$ derivatives were reported to display two smectic phases, over a narrow temperature range with the following phase diagrams, respectively:

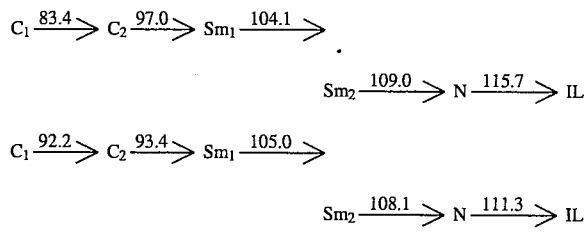

where C=crystal, N=nematic, Sm=smectic and IL=isotropic liquid and temperatures are in ° C. Barrall et al. supra reports that $Sm_1$ appears to be a "tilted smectic B phase" and speculates that $Sm_2$ is a smectic C phase. Grant supra (1978) also reports the para-substituted phenylacetylenes:

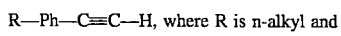

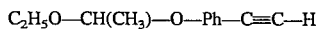

which are employed in the synthesis of the alkyl- and alkoxy-substituted diphenyldiacetylenes.

Gray et al. (1989) WO 89/02425 refers to laterally fluorinated oligophenyls useful as liquid crystals which are biphenyls or terphenyls. Formula III of the reference, refers to tolanes, i.e.,:

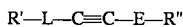

where laterally fluorinated 1,4-benzene rings are included in the listing of L and E. Formula 3.1 refers to a monofluorinated tolane of formula:

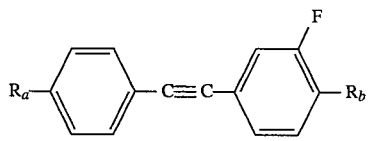

where $R_a$ and $R_b$ may be alkyl or alkoxy.

Higuchi et al. U.S. Pat. No. 4,728,458 refers to chiral polyphenyl compounds useful in liquid crystal materials. The general formula (1) in the reference refers to halogenation of the core moiety which core appears to include tolanes: —Ph—C≡C—Ph—. However, no tolanes appear to be specifically disclosed therein.

Eidenschink et al. WO 87/05018 refers to optically active compounds and the general formula I in the reference appears to refer to cores containing halogenated 1,4-phenylene groups and appears to refer to tolane cores. A related application of Krause et al. WO 86/06373 refers in formula I to halogenation of cores containing nitrogen containing heterocycles.

Saito et al. (1988) EP published application 278,665 refers to chiral 2-substituted alkyl ethers useful as components in LC compositions which include those having 3,3'-halogenated biphenyl cores.

German laid-open application DE3901266 discloses certain fluorinated diphenyldiacetylenes and tolanes having the formula:

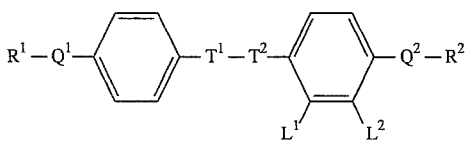

in which $R^1$ is 1–12 C alkyl, or 2–12 C alkenyl, $Q^1$ and $Q^2$ are an O, or a single bond and one of $Q^1$ or $Q^2$ may be a trans-1,4-cyclohexylene; $T^1$ or $T^2$ can be —C≡C— or $CH_2CH_2$-Phe-, where Phen=1,4, -phenylene; $R^2$=F, Cl, $CF_3$, $OCHF_2$ or $R^1$ and one of $L^1$ and $L^2$=F and the other of $L^1$ and $L^2$=H or F. These compounds are said to be useful as liquid crystal or mesogenic compounds having extremely high optical anisotropy.

Reiffenrath et al. (1989) Liq. Cryst. 5(1):159–170 refers to certain liquid crystalline compounds having 1,4-disubstituted-2,3-difluorobenzene groups having negative dielectric anisotropy. Specifically disclosed are two difluorinated tolanes:

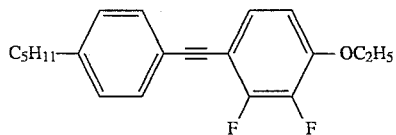

and

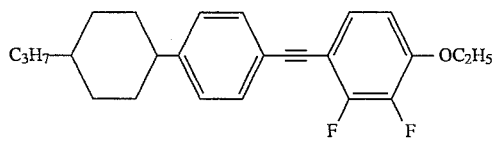

EP application 383621, CA abstract (101) 424111s refers to diphenyldiacetylene compounds having trifluoromethyl substituents which are useful in the preparation of polymers.

JP 59046233 (Abstract in English) refers to compounds of formula: R—C≡C—C≡C—R where R is a 2-$CF_3$–$C_6H_5$, or a 2,4-, 2,5-, or 3,5-$(CF_3)_2$—$C_6H_4$ group, which are useful in polymer preparation.

SUMMARY OF THE INVENTION

The present invention provides compounds useful in liquid crystal compositions that are halogenated diphenyldiacetylenes of the general formula:

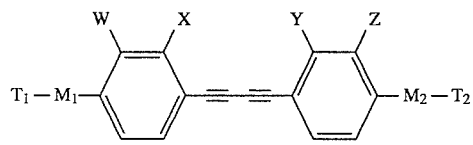

where W, X, Y and Z are, independently of one another, a halogen atom, a trihalomethyl group or a hydrogen atom, wherein each phenyl ring is substituted with at least one halogen atom or trihalomethyl group, where $T_1$ and $T_2$, independently of one another, are alkyl, alkenyl, alkoxy, ether, haloalkyl, haloalkylether, thioalkyl or thioalkenyl tail groups having from three to twenty carbon atoms or silylalkyl, silylalkenyl, silylalkoxy or silylthioalkyl groups having from three to twenty-eight carbon atoms and where $M_1$ and $M_2$, independently of one another can be a single bond or one of $M_1$ or $M_2$ can be a trans-1,4-cyclohexylene or a —$(CH_2)_2$-trans-1,4-cyclohexylene. The tail groups may contain straight-chain or branched alkyl or alkenyl portions. Specifically, W, X, Y and Z may be F, Cl or $CF_3$. More specifically, W=Z and X=Y or W=X=Y=Z.

$T_1$ and $T_2$, independently of one another, can be $R_1$, $OR_2$, or $SR_3$ tail groups in which $R_1$, $R_2$ and $R_3$ can be straight-chain or branched alkyl or alkenyl groups having from three to twenty carbon atoms wherein one or more non-neighboring carbon atoms can be substituted with an O, S or silylalkyl group except that the C-1 carbon of an $OR_2$ or $SR_3$ tail cannot be substituted by an O, S or silyl alkyl group. Specifically provided are compounds in which $R_1$, $R_2$ or $R_3$ are ω-monoenes. Also specifically provided are compounds in which a dialkylsilyl group is substituted into the $R_1$, $R_2$ or $R_3$ tail group. Compounds having dialkylsilyl groups in which the alkyl group contains 1 to 4 carbon atoms are specifically provided. Compounds in which a dimethylsilyl group is substituted into $R_1$, $R_2$ or $R_3$ groups are provided. Carbon atoms of the $R_1$, $R_2$ and $R_3$ groups can be substituted with one or more halogen atoms, particularly fluorine atoms, except that the C-1 carbon of an $OR_2$ or $SR_3$ tail may not be halogenated.

Tail groups, $T_1$ and $T_2$ of the compounds of the present invention include but are not limited to:

alkyl, alkenyl, alkoxy, alkenoxy, thioalkyl and thioalkenyl, including: $R_A$, $R_B$, $OR_A$, OR, $SR_A$ and $SR_B$ where $R_A$ is an alkyl group having 3–20 carbon atoms and $R_B$ is an alkenyl group having 3–20 carbon atoms;

ethers, including: $R_n$—O—$R_m$ where $R_n$ and $R_m$ are alkyl or alkenyl portions, having n and m carbon atoms, respectively where n+m=3–20 carbon atoms;

silylalkyl, silylalkenyl, silylalkoxy and silylthioalkyl, including: $R_{Si}$, O—$R_{Si}$ and S—$R_{Si}$, where $R_{Si}$ is more generally $R_n$—$Si R_C$—$R_m$ in which $R_n$ and $R_m$ are alkyl or alkenyl portions having n and m carbon atoms, respectively, and n+m=3–20 and in which $R_C$ and $R_D$ are alkyl or alkenyl groups having 1 to 4 carbon atoms and more specifically where $R_{Si}$ is —$(CH_2)_n$—$SiR_C R_D$—$(CH_2)_{m-1}$ $CH_3$ or —$(CH_2)_n$—$Si(CH_3)_2$—$(CH_2)_{m-1}$ $CH_3$, where n+m=2–19;

haloalkyl, haloalkylethers, haloalkoxy groups, including: $R_F$ and $OR_F$, where $R_F$ is an alkyl group having 3–20 carbons in which one or more of the carbons is substituted with a fluorine atom; O—$(CH_2)_n$—$(CF_2)_m$—$CF_3$ or —O—$(CH_2)_n$—$(CF_2)_m$—$CF_2H$, where n=1–19; —O—$(CH_2)_n$—O—$(CF_2)_m$—$CF_2H$ or —O—$(CH_2)_n$—O—$(CF_2)_m$—$CF_3$, where n+m=2–19; or —O—$(CH_2)_n$—O—$(CH_2)_m$—$(CF_2)_f$—$CF_2H$ or, —O—$(CH_2)_n$—O— $(CH_2)_m$—$(CF_2)_f$—$CF_3$, —O—$(CH_2)_n$—$(CF_2)_m$—O— $(CF_2)_f$—$CF_2H$ or —O—$(CH_2)_n$—$(CF_2)_m$—O—$(CF_2)_f$— $CF_3$ where n+m+l= 3–19.

Preferred $R_A$, $R_B$, and $R_F$ groups have from 5 to 12 carbon atoms; Preferred $R_{Si}$ groups have from 7 to 16 carbon atoms; Preferred $R_C$ and $R_D$ are methyl groups.

This invention provides compounds of formula A in which W, X, Y and Z are all fluorine atoms and in which $T_1$, $T_2$, $M_1$ and $M_2$ are as defined above. Specifically provided are those tetrafluorinated diphenyldiacetylenes in which $T_1$ and $T_2$ are alkoxy groups and in which $M_1$ and $M_2$ are single bonds.

This invention provides compounds of formula:

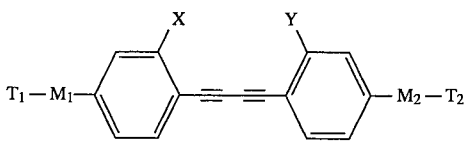

where X and Y, independently of one another, are a halogen atom or a trihalomethyl group wherein $T_1$, $T_2$, $M_1$ and $M_2$ are as defined above. In particular, compounds in which X and Y are both fluorine atoms, both chlorine atoms or both trifluoromethyl groups, $T_1$ and $T_2$ are alkyl, alkoxy, alkenyl or alkenoxy groups and $M_1$ and $M_2$ are both single bonds, are provided.

This invention also provides compounds of formula:

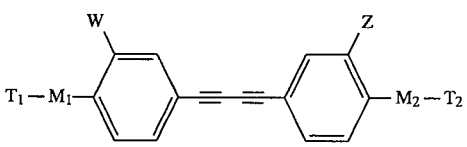

where W and Z, independently of one another, are a halogen atom or a trihalomethyl group and wherein $T_1$, $T_2$, $M_1$ and $M_2$ are as defined above. In particular, compounds in which W and Z are both F are provided. Difluorinated diphenyldiacetylenes of formula C in which $T_1$ and $T_2$ are alkyl or thioalkyl groups and $M_1$ and $M_2$ are both single bonds, are specifically provided.

In addition, compounds of formula C in which $T_1$ and/or $T_2$ are haloalkylethers, particularly fluoroalkylethers such as those in which $T_1$ and/or $T_2$ can be:

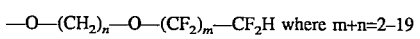

—O—$(CH_2)_n$—O—$(CF_2)_m$—$CF_2H$ where m+n=2–19 and, more particularly, those compounds in which n=2 and m=3 are provided.

Further, this invention provides compounds of formula:

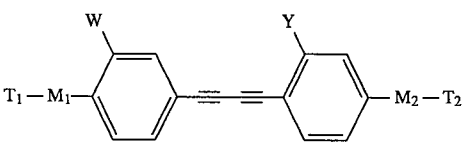

where W and Y, independently of one another, are a halogen atom or a trihalomethyl group and wherein $T_1$, $T_2$, $M_1$ and $M_2$ are as defined above. In particular, compounds in which both W and Y are F are provided. Compounds of formula D in which $T_1$ and $T_2$ are alkyl, alkenyl, alkoxy or alkenoxy groups and $M_1$ and $M_2$ are both single bonds are specifically provided.

Yet further, this invention provides compounds of formula:

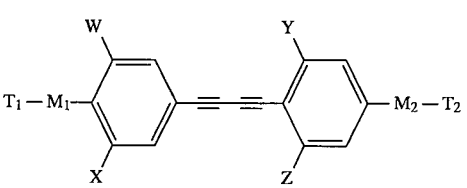

where W, X, Y and Z, independently of one another, are a hydrogen atom, a halogen atom or a trihalomethyl group wherein each phenyl ring is substituted with at least one halogen atom or trihalomethyl group and wherein $T_1$, $T_2$, $M_1$ and $M_2$ are as defined above. Compounds in which all of W, X, Y and Z are halogens are provided and, in particular, compounds where all of W, X, Y and Z are F are provided. Compounds of formula E in which $T_1$ and $T_2$ are alkyl, alkenyl, alkoxy or alkenoxy groups and $M_1$ and $M_2$ are both single bonds are specifically provided.

Compounds of formulas A–E in which one of $M_1$ or $M_2$ is a trans-1,4-cyclohexylene group or a —$CH_2CH_2$-trans-1,4-cyclohexylene group, e.g. having the formulas:

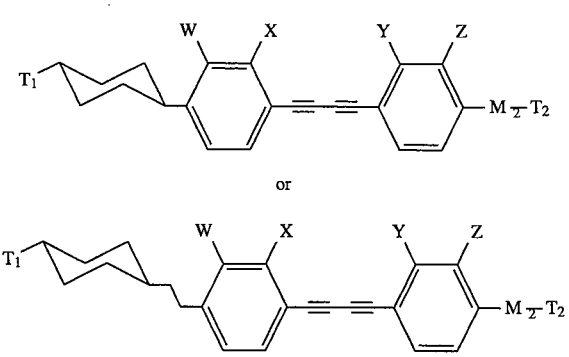

or are provided. Difluoro- and tetrafluorodiphenyldiacetylenes of formulas A–E where one of $M_1$ or $M_2$ is a trans-1,4-cyclohexylene group or a —$CH_2CH_2$—trans-1,4-cyclohexylene group and the other of $M_1$ or $M_2$ is a single bond and $T_1$ and $T_2$ are alkyl, alkoxy, alkenyl or alkenoxy groups are specifically provided.

Tail groups $T_1$ or $T_2$ or both $T_1$ and $T_2$ of the compounds of formulas A, B, C, D or E may be chiral, non-racemic groups.

The present invention provides liquid crystal compositions containing one or more of the compounds of formulas A–E.

The compounds of the present invention are generally useful as liquid crystal materials or as components of liquid crystal materials.

Compounds of the present invention are useful alone or in combination with one another or with other liquid crystal components to provide nematic LC materials, including super twist nematics, FLC host materials or FLC materials. Compounds of this invention can, for example, be admixed to prepare mixtures having more desirable mesomorphic properties, i.e., nematic phases, broader smectic C phases and/or smectic C phases close to room temperature.

FLC host materials comprising one or more of the compounds of this invention can be admixed with any of a variety of FLC dopants to prepare FLC materials having fast switching speeds. In particular, materials comprising about 50% or more by weight of a mixture of one or more of the components of this invention and substantially retaining a smectic C phase preferably extending over a range of 5° C. or more will be useful as FLC hosts.

The compounds of the present invention are also useful as components of liquid crystals, particularly nematic and FLC materials to increase the birefringence of the resulting mixture. In particular, the diphenyldiacetylenes of the present invention are useful for increasing birefringence in mixtures which retain desirable mesomorphic properties, i.e., smectic C phases or nematic phases. Certain compounds of the present invention can be employed to produce LC compositions with birefringence greater than or equal to 0.3.

High birefringence nematic liquid crystals and ferroelectric liquid crystals of the present invention preferably contain from about 5% to about 30% by weight of a mixture of one or more of the compounds of formulas A, B, C, D or E.

Compounds of formulas D and E of the present invention and particularly those in which W and Y are F or W, X, Y and/or Z are F are also useful as components of liquid crystals with positive dielectric anisotropy. These compounds can impart high birefringence to liquid crystal mixtures along with positive dielectric anisotropy. Nematic LC compositions of this invention include those with positive dielectric anisotropy and high birefringence which contain from about 5% by weight to about 30% by weight of a mixture of one or more of the compounds of formulas D and/or E.

DETAILED DESCRIPTION OF THE INVENTION

The 4,4'-disubstituted halogenated diphenyldiacetylenes of the present invention are prepared as exemplified in Schemes I–III.

Generally, as shown in Scheme I, an appropriately substituted phenylbromide, such as 2, is coupled to a protected acetylene (a TMS-protected acetylene is exemplified) to give a desired 4-substituted-3-halophenylacetylene (such as 4). Two molecules of the phenylacetylene are then coupled to produce a diphenyldiacetylene (such as 5).

In related Scheme II, an appropriately alkyl substituted phenylbromide, such as 8, is coupled to a protected acetylene (dimethylcarbinol protection is exemplified) using a palladium catalyst to give a protected phenylacetylene 9. Deprotection, here under basic conditions, results in the phenylacetylene 10. The phenylacetylene is then self-condensed as in Scheme I to give the desired dialkyldiphenyldiacetylene 11. The alkyl-substituted phenylbromide starting material 8 is prepared, for example, by reaction of the benzylbromide 7 with an alkyl Grignard reagent. The benzylbromide 7 can be prepared by reaction of bromofluorotoluene 6 with N-bromosuccinimide (NBS).

Related Scheme III exemplifies the synthesis of dithiodiphenyldiacetylenes (16). The substituted phenol is converted in three steps to the thiophenol 13. The phenol is initially treated with N,N-dimethyl-thiocarbamoyl chloride to give a thiocarbamate which is thermally rearranged to the thiophenylcarbamate 12. Hydrolysis of 12 gives the bromothiophenol 13. The bromothiophenol is alkylated to give the bromophenyl alkylthioether 14. As in Scheme II, the bromophenyl alkylthioether is reacted with protected acetylene to give a protected phenylacetylene which is deprotected to give the phenylacetylene 15. Self-condensation of the thioetherphenylacetylene gives a dithioalkyldiphenyldiacetylene 16.

R in Schemes I–III can be any of $R_1$, $R_2$, $R_3$, $R_A$, $R_B$, $R_F$ or $R_{Si}$ as defined above.

The compounds of this invention of formulas A–E can be readily synthesized by the methods of Schemes I–III or by routine adaptation of those methods in view of well-known techniques and the descriptions provided in this specification. Choice of starting materials, reagents, protecting agents and reaction conditions needed to synthesize the various compounds of this invention are routine and within the ordinary skill in the art.

For example, the 2,2'-difluorodiphenyldiacetylenes, the 3,3'-dichlorodiphenyldiacetylenes, the 2,2'-dichlorodiphenyldiacetylenes and the 2,2'-bis-trifluoromethyldiphenyldiacetylenes of this invention can be prepared by the methods of Schemes I–III by appropriate choice of starting phenols or toluenes. The various $T_1$ and $T_2$ tails of this invention can be introduced onto halogenated diphenyldiacetylene cores of this invention using the methods of Schemes I–III and routine modifications of those methods.

Fluorocarbon/hydrocarbon ether tails, such as $HCF_2CF_2CF_2CF_2CH_2$—O—$CH_2$—$CH_2$—O—, can be introduced into the diphenyldiacetylene cores of this invention by well-known techniques, such as those described in Scheme I, or by employing the fluorocarbon/hydrocarbon ether tosylate and methods described in Chiang et al. (1991) Mol. Cryst. Liq. Cryst. 208:85–98 and Adams et al. (1990) Mol. Cryst. Liq. Cryst. 183B:257–267, and routine modifications of those methods.

A variety of alkyl, alkenyl, alkylether, silylalkyl and haloalkyl groups can be readily substituted for RO in Scheme I and RS in Scheme III. For example, an ω-alkeneoxy group can be introduced in a compound of formula 2 by use of the ω-alkeneol as ROH.

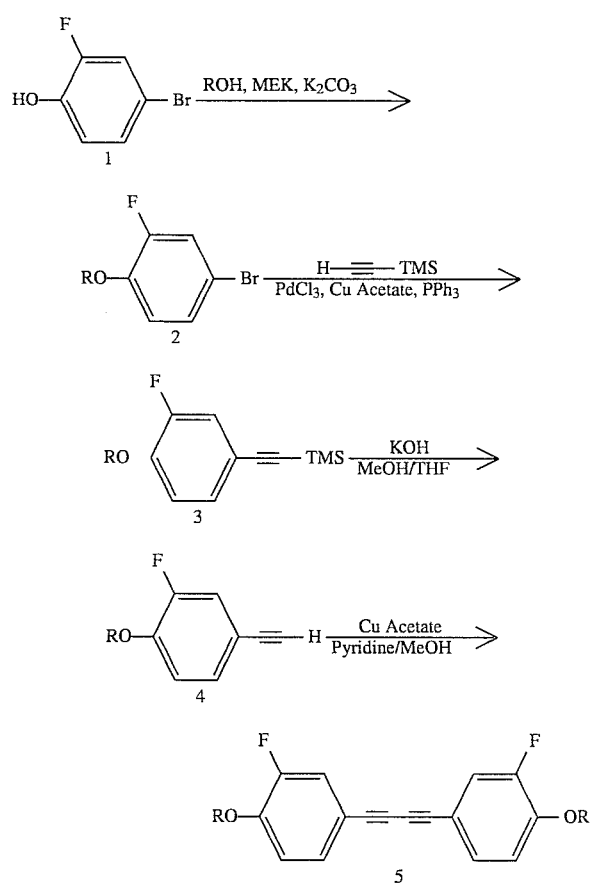

SCHEME I

SCHEME II
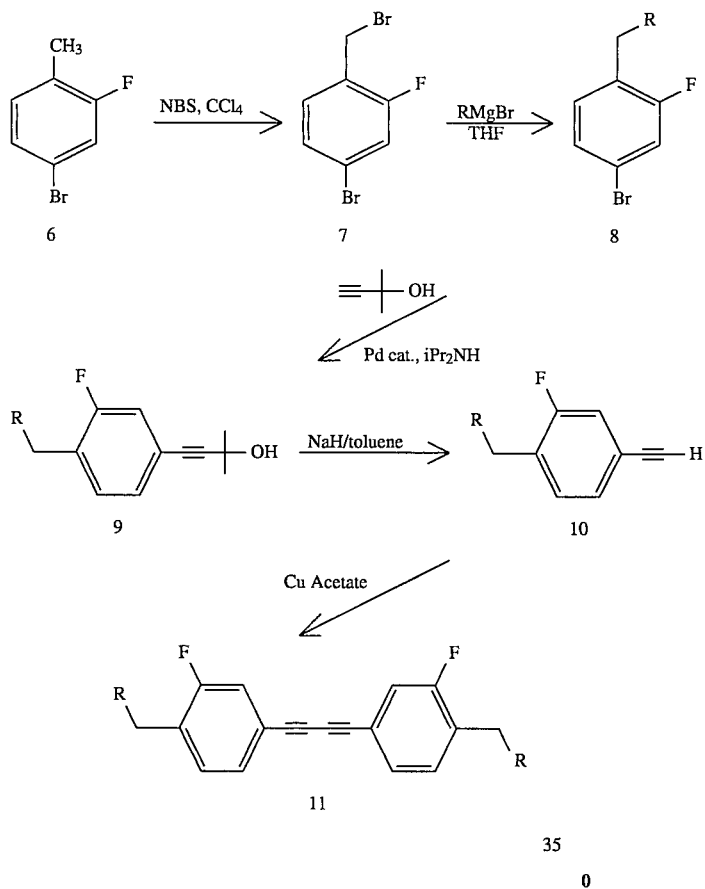
SCHEME III
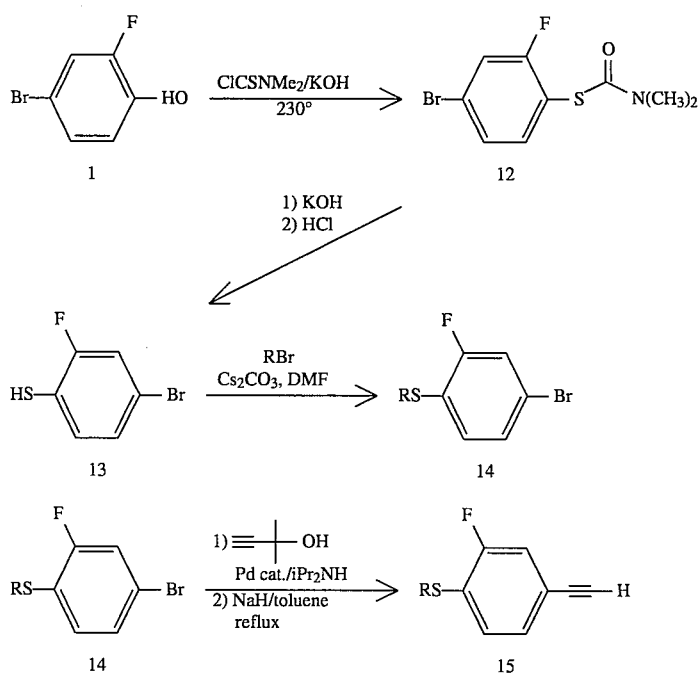

SCHEME III

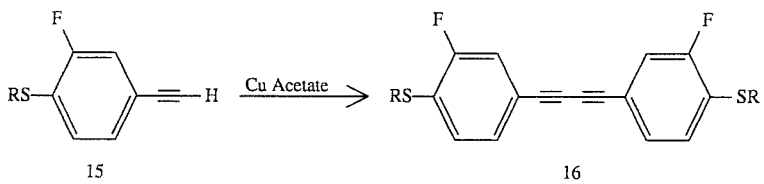

Compounds of formulas A–E which include a trans-1,4-cyclohexenyl group can be synthesized by well-known methods or by routine adaptation of such well-known methods in view of the descriptions provided herein.

Those of ordinary skill in the art will appreciate that other methods can be applied or readily adapted to the synthesis of compounds of formulas A, B, C, D and E. For example, the methods of Grant (1978) supra and methods referred to therein may be employed or readily adapted, in particular to the synthesis of symmetric diphenyldiacetylenes. Several methods of synthesis of unsymmetric diphenyldiacetylenes, which include for example, compounds C where $T_1 \neq T_2$ and $M_1$ and $M_2$ both are single bonds, have been reported. (See: H. Shindo et al. (1990) J. Chem. Soc. Chem. Comm. 760, J. Tsibouklis et al. (1988) Chemtronics 3:211 and G. W. Milburn et al. (1990) Liq. Crystals 8:623–627.) Such methods can be readily adapted by choice of reagents or starting materials or the preparation of compounds of the present invention.

Nematic liquid crystal can be a single component or, more typically, mixtures of components. Nematic liquid crystals need not contain chiral nonracemic components. Nematic LCs preferred for device applications have broad nematic phases spanning room temperature. LC components can be added to nematic LCs to enhance or change their electro-optic properties including dielectric anisotropy and birefringence. Suitable components are those that are compatible for mixing with a given nematic LC and which do not have significant detriment on the mesomorphic properties of the mixture.

FLC materials are chiral nonracemic materials which exhibit a chiral tilted smectic phase, preferably a smectic C* phase. Such materials may be composed of a single chiral nonracemic FLC or may be a mixture of components. For example, a chiral nonracemic FLC dopant can be mixed with an FLC host which exhibits a smectic C phase to produce a chiral nonracemic FLC material. Such FLC materials are useful in optical devices such as those described by Clark and Lagerwall (supra), Surface Stabilized Ferroelectric Liquid Crystal Cells (SSFLC). FLC materials preferably display a fast switching speed in such devices. It is preferred that the FLC materials display a smectic C* phase. It is also preferred that the FLC materials do not exhibit higher order smectic phases. For use in such devices, it is preferred that the smectic C* phase extend at least over about 5° C. It is more preferred that the smectic C* phase extend over about 20° or more. A material having a smectic C* phase close to room temperature is desirable for use in devices which are intended for use at or near room temperature (20°–25° C.). It is most desirable in such applications to have a material which displays a smectic C* phase; the temperature range of which spans room temperature.

FLC hosts are single compounds or multi-component mixtures which may or may not be chiral and nonracemic. Generally, FLC host materials exhibit a smectic C phase. If chiral and nonracemic, an FLC host generally has low polarization density. Chiral nonracemic FLC dopants, compatible for mixing with the host, are added to enhance the polarization density and decrease switching speed of the mixture. A variety of chiral nonracemic FLC dopants have been described. Dopants are admixed with the FLC host at a level which maximizes the polarization density of the resultant mixture, without significant adverse effect on the desired phase (or other) properties of the resultant mixture. For example, significant narrowing of the smectic C phase is generally to be avoided. Significant shifting of the smectic C phase away from room temperature for applications at or near room temperature is undesirable. The phase properties of the resultant FLC mixtures are most preferably thermodynamically stable. The amount of a dopant which can be added to a particular host material also depends on the solubility or miscibility of the dopant in the host.

The mesomorphic and other properties (including tilt angle, birefringence and switching speed) of an FLC material can be adjusted for use in a particular application by addition of components to a mixture or by adjusting the concentration of components in the mixture.

Examples of FLC dopants include, among others, those with phenylpyridine, phenylpyrimidine, and phenylbenzoate cores as described, for example, in: Walba and Vohra U.S. Pat. Nos. 4,705,874 and 4,638,073; Walba and Razavi U.S. Pat. No. 4,695,650; Walba and Eidman U.S. Pat. No. 4,777,280; Sakaguchi et al U.S. Pat. Nos. 4,909,957 and 4,973,425; Hemmerling et al. U.S. Pat. No. 4,876,028.

The diphenyldiacetylene compounds of the present invention are additionally found to impart increased birefringence to nematic and FLC mixtures. Birefringence (or $\Delta n$) of a mixture in the smectic C phase is measured by conventional methods, such as those employing an Abbe Refractometer. For high birefringence applications, a $\Delta n$ of about 0.19 or more is preferred and $\Delta n$ of 0.3 or more is more preferred. Mixtures of diphenyldiacetylenes have $\Delta n$ ranging from about 0.30 to 0.34. Diphenyldiacetylenes of the present invention can be admixed with compatible FLC materials and hosts or compatible nematic LCs to achieve high birefringence materials.

In particular, the fluorinated and trifluoromethyl-substituted phenylacetylenes of the present invention are useful as components to increase birefringence of nematic LC and FLC material.

The dithiodiphenyldiacetylenes of this invention, such as MDW447 (Table 3), are particularly useful in applications involving IR modulation since they are more transparent than the analogous alkoxy derivatives in the infra red.

Compounds of this invention having silylalkyl, silylalkenyl, silylalkoxy and silylthioalkyl tail groups are additionally useful in LC compositions to broaden desired smectic C and nematic phases and give better eutectic mixtures.

Similarly, compounds of this invention having fluorocarbon/ether tails, such as O—(CH$_2$)$_2$—O—CH$_2$—(CF$_2$)$_3$CF$_2$H are useful for producing LC mixtures with broad smectic C and nematic phases.

Diphenyldiacetylenes of this invention which are symmetrical, i.e., in which W=Z, X=Y, T$_1$=T$_2$, and M$_1$ and M$_2$ are both single bonds, are generally preferred for use in liquid crystalline applications over their unsymmetric analogous. The symmetrical diphenyldiacetylenes generally are easier to align properly for device applications.

The compounds of formula D and E in which W and Y or W, X, Y and Z are halogens, and particularly those in which the halogen is fluorine, will have positive dielectric anisotropy due to the presence of a longitudinal dipole in the diphenyldiacetylene core. Compounds with positive dielectric anisotropy are useful in preparation of liquid crystal compositions with positive dielectric anisotropy, particularly for active addressing applications in STN devices. Compounds of formulas D and E will, in addition, display high birefringence.

EXAMPLES

Example 1

Synthesis of 4-alkoxyl, 3-fluorophenyl Acetylenes IV

The synthesis of the aromatic acetylene compounds of formula 4 (Scheme I) are exemplified by the following synthesis of compound 4, where R is C$_{10}$H$_{21}$.

To a 50 ml round bottom flask was added 2.77 g (12.5 mmoles) 1-bromodecane and 2.39 g (12.5 mmoles) 2-fluoro-4-bromophenol (1) in 25 ml methyl ethyl ketone. 4.30 g anhydrous potassium carbonate was added and the heterogeneous mixture was refluxed for 48 hrs. The reaction mixture was partitioned between ethyl ether and water, washed with brine, dried, filtered through a 2 inch plug of silica, and solvent removed to afford 4.11 g (99%) of the 4-decyloxy-3-fluorophenyl bromide (2), where R=C$_{10}$H$_{21}$, as a pale yellow clear oil.

To a 250 ml round bottom flask equipped with magnetic stirrer and condenser was added 4.11 g of the 4-decyloxy-3-fluorophenyl bromide in 80 ml dry diisopropylamine. The palladium catalyst (PdCl$_3$, CuAc, PPh$_3$) (118 mg) followed by 1.453 g of trimethylsilyl acetylene was then added and the reaction refluxed for 48 hours. The reaction mixture was partitioned between hexane and water and the organic layer washed with water, brine, and dried with anhydrous magnesium sulfate. Removal of the solvent afforded 4.40 g of a brown oil. Flash chromatography (2% ethyl acetate/hexane) gave 4.11 g (96%) of TMS-protected acetylene (3), where R=C$_{10}$H$_{21}$, as a clear oil.

To a 250 ml round bottom flask equipped with a magnetic stirrer was added 4.11 g (11.8 mmoles) TMS-protected aromatic acetylene (3) and 2.0 g (35.4 mmoles) KOH in 120 ml of 1:1 MeOH/THF. The reaction mixture was stirred overnight at room temperature. After partitioning between diethyl ether and water, the organic phase was sequentially washed with water- and brine and then dried with anhydrous magnesium sulfate affording 3.42 g of aromatic acetylene (4, where R=C$_{10}$H$_{21}$) 4-decyloxy-3-fluorophenylacetylene, as a rust colored oil.

Example 2

Synthesis of 4,4'-Dialkoxy-3,3'-difluoro diphenyldiacetylene (5)

The synthesis of the diphenyldiacetylenes of formula 5 (Scheme I) are exemplified by the following synthesis of compound 5, where R=C$_{10}$H$_{21}$.

To a 50 ml round bottom flask equipped with a magnetic stirrer and reflux condenser was added 300 mg 4-decyloxy-3-fluorophenylacetylene and 43 mg cupric acetate in 40 ml 1:1 pyridine/MeOH. The reaction mixture was refluxed for 2 hrs, allowed to cool to room temperature and then added dropwise into a stirred 9M aqueous sulfuric acid solution at ice bath temperature. The resulting cream-like suspension was extracted with ethyl ether and sequentially washed with water (3×) and brine and dried with anhydrous magnesium sulfate yielding 289 mg of a yellow-brown solid. Flash chromatography (1% ethyl acetate/hexane) and recrystallization of the residue from 95% ethanol afforded 248 mg diphenyldiacetylene (5), 4,4'-didecyloxy-3,3'-difluoro diphenyldiacetylene, as pale yellow needles.

Example 3

Mesomorphic Properties of 3,3'-Difluoro-diphenyldiacetylenes (5)

The phase diagrams of compounds of formula 5 where R= C$_6$H$_{13}$, C$_8$H$_{17}$, C$_9$H$_{19}$, C$_{10}$H$_{21}$, C$_{11}$H$_{23}$, C$_{12}$H$_{25}$ and C$_{14}$H$_{29}$ are provided in Table 1. In this Table and elsewhere in this application, except as noted, the following designations are employed: I=isotropic liquid, N=nematic, C=smectic C and X=crystal and transition temperatures are given in ° C. Phase transition temperatures and the nature of the phase transition were determined using Mettler Differential Thermal Analysis and optical polarized transmission microscopy.

Table 2 provides phase diagrams of nonhalogenated 4,4'-dialkoxydiphenyldiacetylenes (see Barrall et al. (1978) supra), for comparison to Table I. The didecyloxy substituted compound of Table II was prepared by methods analogous to those employed by Grant (1978) supra and phase diagrams were determined as noted above.

The compound of formula C where W=Z=Cl and T$_1$=T$_2$= C$_{10}$H$_{21}$O, 4,4'-decyloxy-3,3'-dichlorodiphenyldiacetylene was synthesized by procedures analogous to those described in Scheme I and examples 1 and 2. The dichlorinated compound exhibited the following phase diagram:

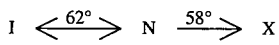

having a narrow nematic phase and no observable smectic C phase.

The 2,2'-dihalogenated analogs of the compounds of formula B, 4,4'-didecyloxy-2,2'-difluoro diphenyldiacetylene and 4,4'-didecyloxy-2,2'-dichloro diphenyldiacetylene were synthesized by methods analogous to those exemplified in Scheme I and Examples 1 and 2. The 2,2'-difluoro compound exhibited the following phase diagram:

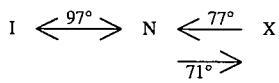

This compound exhibits a 20° C. enantiotropic nematic phase and no smectic phases were observed.

TABLE 1

| MDW # | Alkoxy Tail R—O— | Mesomorphic Properties of 3,3'-difluorinated diphenyldiacetylenes 5 (Scheme I) |
|---|---|---|
| 328 | $C_6H_{13}O$ | I $\xleftrightarrow{97°}$ N $\xrightarrow{56°} \xleftarrow{71°}$ X |
| 329 | $C_8H_{17}O$ | I $\xleftrightarrow{92°}$ N $\xrightarrow{48°} \xleftarrow{61°}$ C $\xleftrightarrow{46°}$ X |
| 332 | $C_9H_{19}O$ | I $\xleftrightarrow{88°}$ N $\xrightarrow{57°} \xleftarrow{63°}$ C $\xleftrightarrow{49°}$ X |
| 308 | $C_{10}H_{21}O$ | I $\xleftrightarrow{88°}$ N $\xrightarrow{60°}$ C $\xrightarrow{40°} \xleftarrow{54°}$ X |
| 333 | $C_{11}H_{23}O$ | I $\xleftrightarrow{86°}$ N $\xleftrightarrow{69°}$ C $\xrightarrow{41°} \xleftarrow{58°}$ X |
| 324 | $C_{12}H_{25}O$ | I $\xleftrightarrow{86°}$ N $\xleftrightarrow{74°}$ C $\xrightarrow{40°} \xleftarrow{50°}$ X |
| 325 | $C_{14}H_{29}O$ | I $\xleftrightarrow{84°}$ N $\xleftrightarrow{79°}$ C $\xrightarrow{50°} \xleftarrow{59°}$ X |
| 392 | $C_{15}H_{31}O$ | I $\xleftrightarrow{84°}$ N $\xleftrightarrow{82°}$ C $\xrightarrow{56°} \xleftarrow{61°}$ X |
| 393 | $C_{16}H_{33}O$ | I $\xleftrightarrow{85°}$ N $\xleftrightarrow{82°}$ C $\xrightarrow{58°} \xleftarrow{62°}$ X |

TABLE 2

| Alkoxy Tail R—O— | Mesomorphic Properties of non-fluorinated diphenyldiacetylene |
|---|---|
| $C_6H_{13}O^1$ | I $\xleftrightarrow{149°}$ N $\xleftrightarrow{122°}$ X |
| $C_8H_{17}O^1$ | I $\xleftrightarrow{135°}$ N $\xleftrightarrow{109°}$ $Cr_1$ $\xleftrightarrow{72°}$ X |
| $C_{10}H_{21}O^2$ | I $\xleftrightarrow{127°}$ N $\xleftrightarrow{100°}$ $Cr_1$ $\xleftrightarrow{92°}$ X |
| $C_{14}H_{29}O^1$ | I $\xleftrightarrow{116°}$ N $\xleftrightarrow{109°}$ $Sm_2$ $\xleftarrow{104°}$ $Sm_1$ $\xleftarrow{97°}$ $Cr_1$ $\xleftrightarrow{83°}$ X |

[1]B. Grant (1978) Mol. Cryst. Liq. Cryst., 48:175–182.
[2]The present work.

TABLE 3
Phase Diagrams of Exemplary Compounds of Formulas A, B, and C
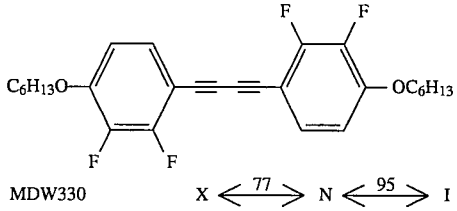
MDW330   X ⇌ 77 ⇌ N ⇌ 95 ⇌ I
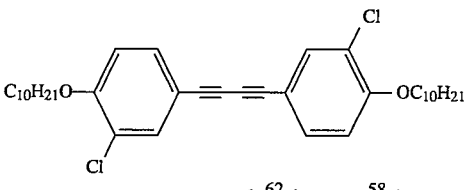
MDW377   I ⇌ 62 ⇌ N —58→ X
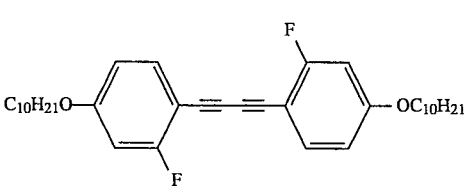
MDW385   I ⇌ 97 ⇌ N ⇌ 77/71 ⇌ X
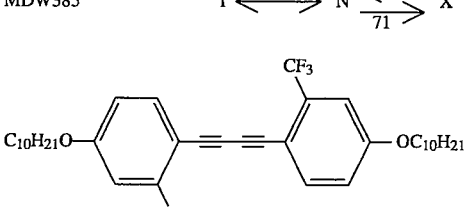
MDW386   I ⇌ 55/24 ⇌ X
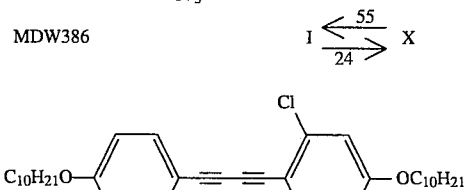
MDW387   I ⇌ 59/65 ⇌ N —56→ X
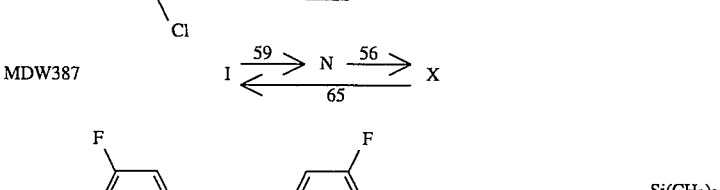
MDW412   I ⇌ 63 ⇌ C ⇌ 51/39 ⇌ X
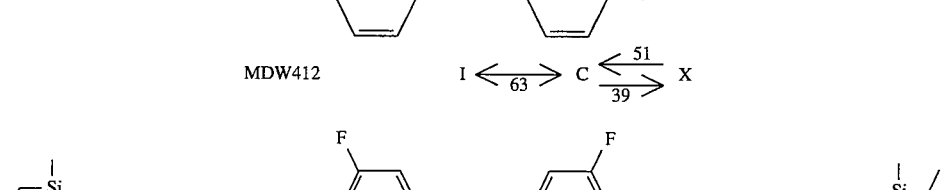
MDW439   I ⇌ 54 ⇌ C ⇌ 42/28 ⇌ X TABLE 3-continued
Phase Diagrams of Exemplary Compounds of Formulas A, B, and C
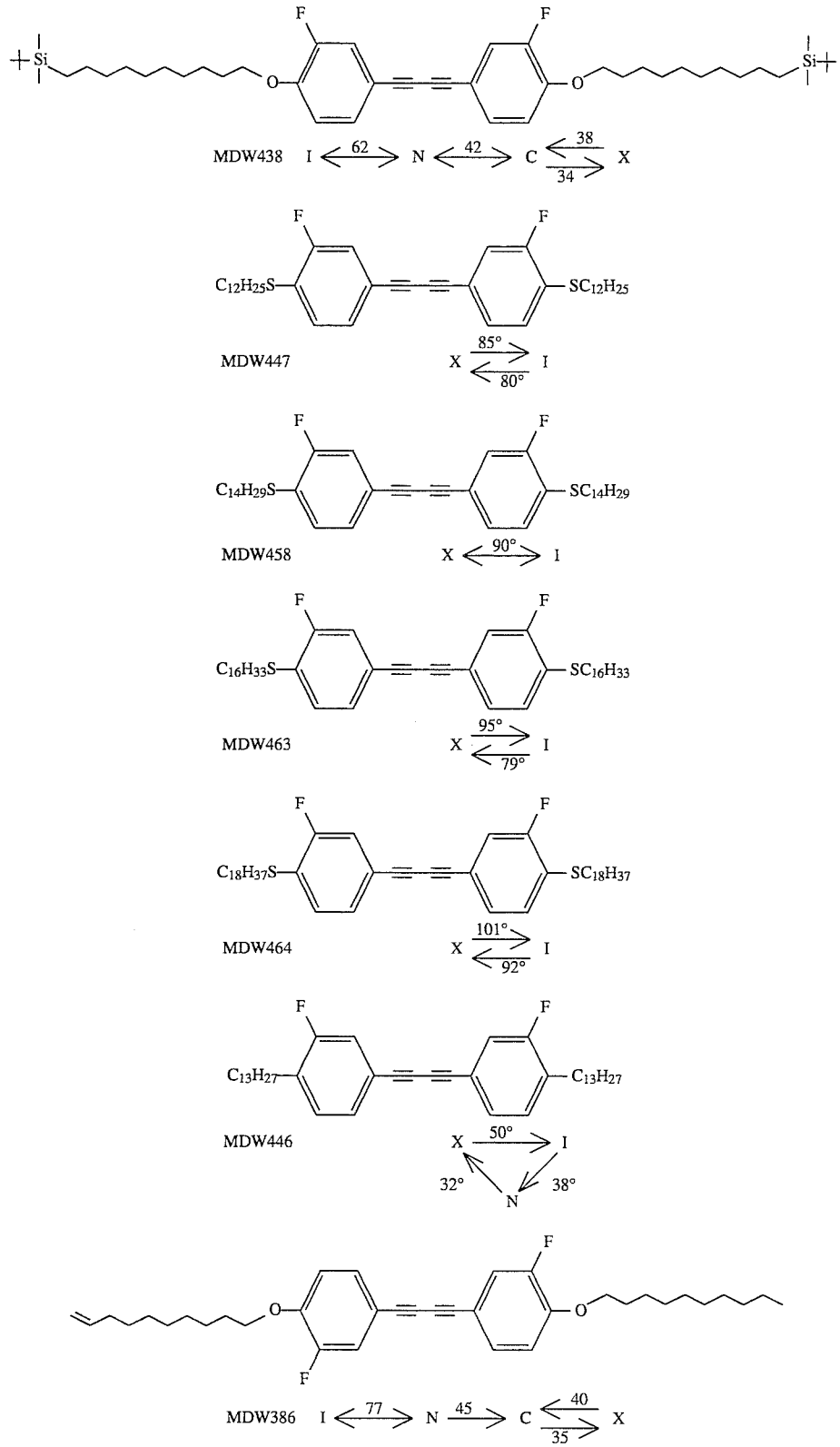

TABLE 3-continued

Phase Diagrams of Exemplary Compounds of Formulas A, B, and C

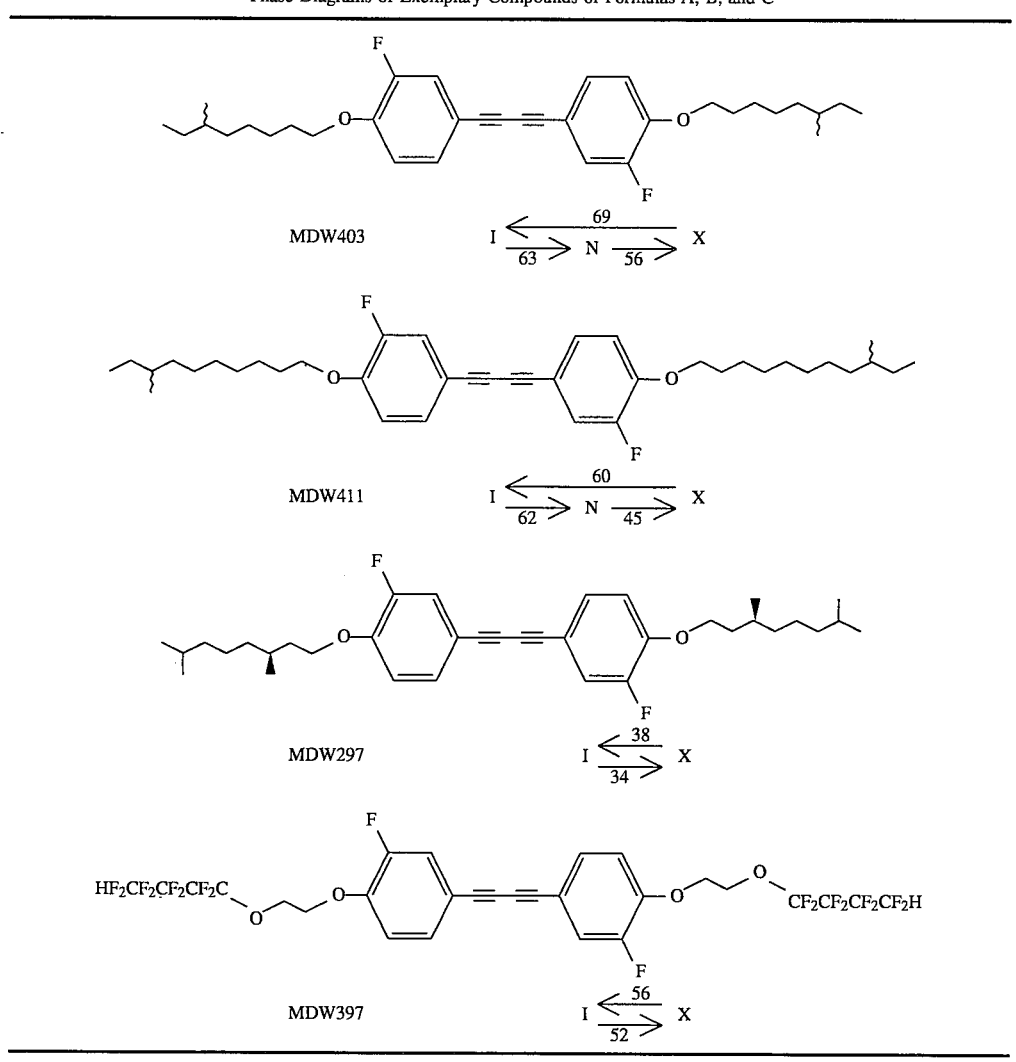

The 2,2'-dichloro compound exhibited the following phase diagram:

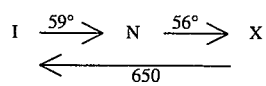

with a 3° C. monotropic nematic phase. The compound of formula C where $T_3=T_4=C_{10}H_{19}$ and $W=Z=F$, 4,4'-didecyl-ω-eneoxy-3,3'-difluorodiphehyldiacetylene was synthesized by methods analogous to those described in Scheme I and Examples 1 and 2. The dialkeneoxy compound exhibited the phase diagram:

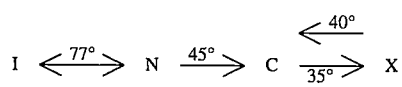

having a smectic C phase.

Example 4

Mesomorphic Properties of Mixtures of Diphenyldiacetylenes

A mixture made from equal parts of the four compounds of formula 5 having $R=C_8H_{17}$, $C_{10}H_{21}$, $C_{12}H_{25}$ and $C_{14}H_{29}$ straight-chain alkyl groups exhibited the phase diagram:

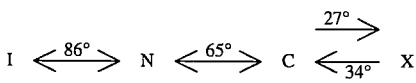

This formulation provides a eutectic mixture with a broad smectic C phase close to room temperature.

Example 5

Mesomorphic Properties of Mixtures of Difluorodiphenyldiacetylenes

A mixture made from equal parts of the five compounds of formula 5 having $R=C_9H_{19}$, $C_{10}H_{21}$, $C_{11}H_{23}$, $C_{12}H_{25}$ and $C_{14}H_{29}$ straight-chain alkyl groups exhibited the phase diagram:

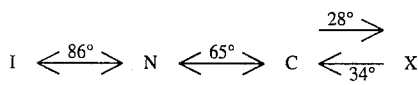

Example 6

Mesomorphic Properties of Mixtures Difluorodiphenyldiacetylenes

A mixture made from equal parts of the three compounds of formula 5 having R=$C_{10}H_{21}$, $C_{11}H_{23}$ and $C_{14}H_{29}$ straight-chain alkyl groups exhibited the phase diagram:

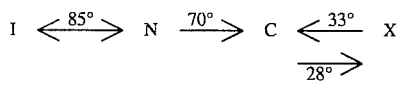

This formulation provides a eutectic mixture with a smectic C phase close to room temperature.

Example 7

Mesomorphic Properties of Mixtures Comprising Difluorodiphenyldiacetylenes of Formula 5

To the mixture of Example 6, 25% by weight of 4,4'-didecyl-ω-eneoxy-3,3'-difluorodiphenyldiacetylene was added. The resultant mixture exhibited the phase diagram:

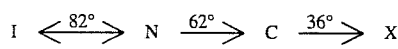

Addition of the dialkeneoxy compound to the mixture of alkoxyl components resulted in a narrowing of the smectic C phase: N→C transition was lowered by about 8° C. and the C→X transition was raised by about 3° C.

25% by weight of 4,4'-didecyloxy-3,3'-dichloro diphenyldiacetylene was added to the mixture of Example 6. The resultant mixture exhibited the phase diagram:

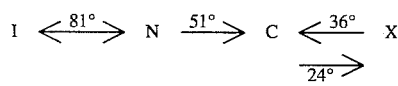

The N→C phase transition was lowered by about 20° C. and the C→X transition was raised by about 1° C.

Three mixtures were prepared by addition of 10% by weight of 4,4'-didecyloxy-2,2'-difluorodiphenyldiacetylene (MDW385), 4,4'-didecyloxy-2,2'-bistrifluoromethyldiphenyldiacetylene (MDW386) or 4,4'-didecyloxy-2,2'-dichloro diphenyldiacetylene (MDW387), respectively, to the mixture of Example 6 also designated MX5595. The resultant mixtures gave the following phase diagrams:

MDW385(10%)/MX5595

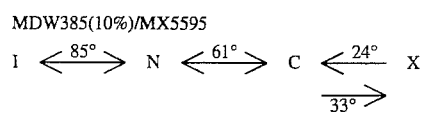

MDW386(10%)/MX5595

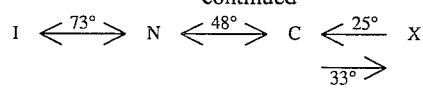

MDW387(10%)/MX5595

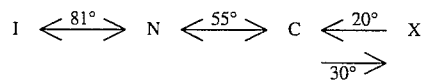

Example 8

High Tilt FLC Mixtures Comprising Difluorodiphenyldiacetylenes

To the mixture of Example 6, 2% (wt/wt, MDW116) a chiral, 2,3-difluoroalkoxylphenylpyrimidine FLC dopant prepared by methods of U.S. Pat. No. 5,051,506. The resultant chiral nonracemic FLC material displayed the phase diagram:

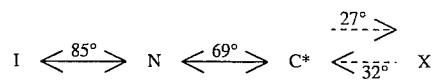

This FLC material was measured to have a tilt angle of 45° in the smectic C* phase.

Example 9

High Birefringence FLC Mixtures Comprising Difluorodiphenyldiacetylenes

CS2004 is a commercially available, high tilt FLC mixture (Chisso). The phase diagram of CS2004 is:

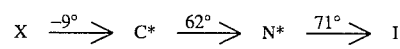

The mixture is believed to contain phenylpyrimidines and biphenylpyrimidines, exhibits a tilt angle of about 44° and was measured to have a birefringence (Δn) of 0.173. A mixture prepared by addition of 30% by weight of the difluorodiphenyldiacetylene mixture of Example 6 to CS2004 exhibited the phase diagram:

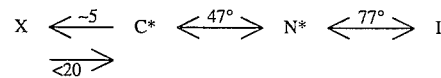

This mixture was measured to have a birefringence of 0.201. This mixture is, thus, a high birefringence, thermodynamically stable, broad C phase room temperature FLC material.

A high birefringence FLC mixture was prepared by combination of 62.5% of the mixture of Example 5, 25% CS2004 and 16.5% of a chiral nonracemic 3-ring tolane, designated MDW295:

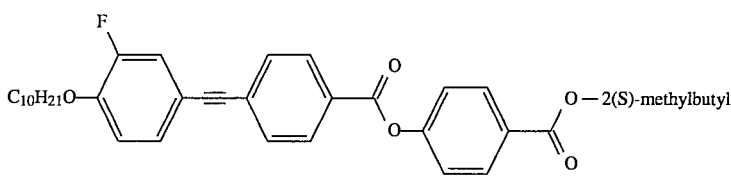

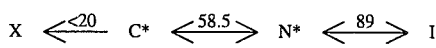

The mixture was found to have a birefringence of 0.245 and to exhibit the phase diagram:

X <—<20—> C* <—58.5—> N* <—89—> I

Example 10

Effect of Addition of Diphenyldiacetylene Dopants on Birefringence and Clearing Point in Nematic Liquid Crystal Compositions Table 4 provides Δn ($n_e$–$n_o$) of mixtures of diphenyldiacetylenes MDW328 and MDW329 in an exemplary nematic liquid crystal host. The host employed in these mixtures is RDK-01160, a commercially available room temperature nematic, believed to be composed primarily of tolane compounds. As seen in Table 4, addition of MDW328 or MDW329 significantly increases the birefringence of the nematic mixtures without significant effect on the clearing point of the mixture.

TABLE 4

Effect of diacetylene dopants on birefringence and clearing point of tolane-based nematic host RDK-01160

| MDW # | % Dopant | $n_e$ | $n_o$ | Δn | 1→N °C. |
|---|---|---|---|---|---|
| RDK-01160 | 0 | 1.708 | 1.506 | 0.202 | 94.5 |
| MDW 328 | 10 | 1.722 | 1.505 | 0.217 | 95.0 |
| MDW 328 | 20 | 1.732 | 1.504 | 0.228 | 95.0 |
| MDW 328 | 25 | 1.737 | 1.504 | 0.233 | 95.0 |
| MDW 329 | 10 | 1.718 | 1.504 | 0.214 | 94.0 |
| MDW 329 | 20 | 1.725 | 1.503 | 0.222 | 94.0 |
| MDW 329 | 30 | 1.731 | 1.501 | 0.230 | 93.0 |

Example 11

Mesomorphic Properties of Exemplary Compounds of Formulas A, B and C

Phase diagrams of a variety of compounds of formulas A, B and C are provided in Table 3. Designations in Table are the same as used in Tables 1 and 2.

Those of ordinary skill in the art will readily appreciate that alternate techniques and procedures and functionally equivalent materials, other than those specifically described herein, can be employed to achieve the goals of the present invention. All such alternatives, variants and functional equivalents are considered to be encompassed by the spirit and scope of this invention.

We claim:

1. A compound of formula:

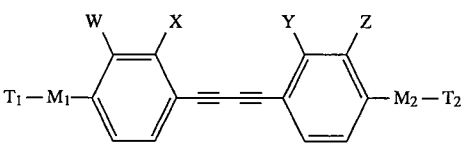

wherein W, X, Y, and Z, independently of one another, is a halogen atom, a hydrogen atom or a trihalomethyl group such that each phenyl ring of the compound is substituted with at least one halogen atom or trihalomethyl group and wherein $T_1$ and $T_2$, independently of one another, can be an alkyl, alkene, alkoxy, alkenoxy, ether, thioalkyl, thioalkenyl, haloalkyl, haloalkoxy or haloalkylether groups having from three to twenty carbon atoms or a silylalkyl, silylalkenyl, silylalkoxy or silylthioalkyl group having from three to twenty-eight carbon atoms and wherein $M_1$ and $M_2$ can both be single bonds or one of $M_1$ or $M_2$ can be a trans-1,4-cyclohexylene or a —$CH_2CH_2$-trans-1,4-cyclohexylene with the exception that when $M_1$ and $M_2$ are both single bonds and $T_1$ and $T_2$ are alkoxy groups, W and Z cannot be fluorine atoms.

2. The compound according to claim 1 wherein W, X, Y and Z are fluorine atoms.

3. The compound according to claim 1 where $M_1$ and $M_2$ are both single bonds.

4. The compound according to claim 3 wherein $T_1$ and $T_2$ are alkyl, alkoxy, alkenyl or alkenoxy groups.

5. The compound according to claim 1 wherein W, X, Y and Z are chlorine atoms.

6. The compound according to claim 1 wherein said trihalomethyl group is a trifluoromethyl group.

7. The compound according to claim 1 wherein $T_1$ and $T_2$ are alkyl, alkene, alkoxy or alkenoxy groups.

8. The compound according to claim 1 wherein $T_1$ and $T_2$ are thioalkyl or thioalkenyl groups.

9. The compound according to claim 1 wherein $T_1$ and $T_2$ are haloalkylether groups.

10. The compound according to claim 8 wherein $T_1$ and $T_2$ are fluoroalkylether groups.

11. The compound according to claim 1 having the formula:

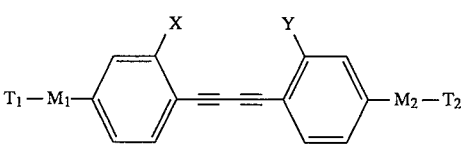

wherein X, and Y, independently of one another, can be a halogen atom, or a trihalomethyl group substituted with at least one halogen atom or trihalomethyl group, wherein $T_1$ and $T_2$, independent of one another, can be an alkyl, alkene, alkoxy, alkenoxy, thioalkyl, thioalkenyl, haloalkyl, haloalkoxy, or haloalkylether group having from three to twenty carbon atoms or a silylalkyl, silylalkenyl, silylalkoxy or silylthioalkyl group having from three to twenty-eight carbon atoms and wherein $M_1$ and $M_2$ are both single bonds.

12. The compound according to claim 11 wherein X and Y are fluorine atoms.

13. The compound according to claim 12 wherein $T_1$ and $T_2$ are alkyl, alkenyl, alkoxy or alkenoxy groups.

14. The compound according to claim 11 wherein X and Y are chlorine atoms.

15. The compound according to claim 14 wherein $T_1$ and $T_2$ are alkyl, alkenyl, alkoxy or alkenoxy groups.

16. The compound according to claim 11 wherein said trihalomethyl group is a trifluoromethyl group.

17. The compound according to claim 16 wherein $T_1$ and $T_2$ are alkyl, alkenyl, alkoxy or alkenoxy groups.

18. The compound according to claim 11 wherein $T_1$ and $T_2$ are alkyl, alkene, alkoxy or alkenoxy groups.

19. The compound according to claim 11 wherein $T_1$ and $T_2$ are thioalkyl or thioalkenyl groups.

20. The compound according to claim 11 wherein $T_1$ and $T_2$ are fluoroalkylether groups.

21. The compound according to claim 1 having the formula:

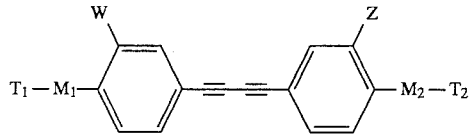

wherein W and Z, independently of one another, can be a halogen atom or a trihalomethyl group and wherein $T_1$ and $T_2$, independently of one another, can be an alkyl, alkene, alkoxy, alkenoxy, ether, thioalkyl, thioalkenyl, haloalkyl, haloalkoxy or haloalkylether group having from three to twenty carbon atoms or a silylalkyl, silylalkoxy or silylthioalkyl group having from three to twenty-eight carbon atoms and wherein $M_1$ and $M_2$ are both single bonds with the exception that when $T_1$ and $T_2$ are alkoxy groups, W and Z cannot be fluorine atoms.

22. The compound according to claim 21 wherein W and Z are fluorine atoms.

23. The compound according to claim 21 where $T_1$ and $T_2$ are thioalkyl or thioalkenyl groups.

24. The compound according to claim 22 where $T_1$ and $T_2$ are thioalkyl groups.

25. The compound according to claim 22 wherein $T_1$ and $T_2$ are alkyl or alkenyl groups.

26. The compound according to claim 22 wherein $T_1$ and $T_2$ are silylalkyl or silylalkoxy groups.

27. The compound according to claim 22 wherein $T_1$ and $T_2$ are fluoroalkylether groups.

28. The compound according to claim 21 wherein W and Z are chlorine atoms.

29. The compound according to claim 28 wherein $T_1$ and $T_2$ are alkyl, alkenyl, alkoxy, or alkenoxy groups.

30. The compound according to claim 21 wherein said trihalomethyl group is a trifluoromethyl group.

31. The compound according to claim 21 wherein $T_1$ and $T_2$ are alkyl, alkene, alkoxy or alkenoxy groups.

32. The compound according to claim 21 wherein $T_1$ and $T_2$ are thioalkyl or thioalkenyl groups.

33. The compound according to claim 21 wherein $T_1$ and $T_2$ are fluoroalkylether groups.

34. The compound according to claim 1 having the formula:

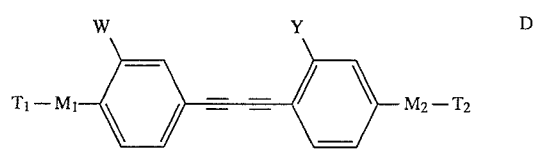

wherein W and Y are both halogen atoms or both trihalomethyl groups, wherein $T_1$ and $T_2$, independently of one another, can be an alkyl, alkenyl, alkoxy, alkenoxy, thioalkyl, thioalkenyl, haloalkyl, haloalkoxy or haloalkylether group having from three to twenty carbon atoms or a silylalkyl, silylalkenyl, silylalkoxy, or silylthioalkyl group having from three to twenty-eight carbon atoms and wherein $M_1$ and $M_2$ are both single bonds.

35. The compound according to claim 34 wherein W and Y are both fluorines.

36. The compound according to claim 34 wherein $T_1$ and $T_2$ are alkyl, alkenyl, alkoxy or alkenoxy groups.

37. The compound having the formula:

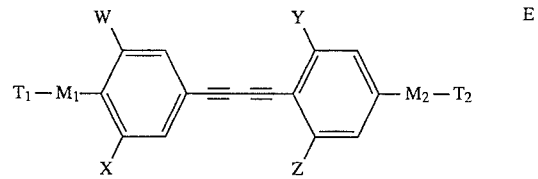

wherein W, X, Y and Z, independently of one another are a halogen or a trihalomethyl group, wherein $T_1$ and $T_2$, independently of one another, can be an alkyl, alkenyl, alkoxy, alkenoxy, thioalkyl, thioalkenyl, haloalkyl, haloalkoxy or haloaklylether group having from three to twenty carbon atoms or a silylalkyl, silylalkenyl, silylalkoxy or silylthioalkyl group having from three to twenty-eight carbon atoms and wherein $M_1$ and $M_2$ are both single bonds.

38. The compound according to claim 37 wherein W, X, Y and Z are all fluorines.

39. The compound according to claim 38 wherein $T_1$ and $T_2$ are alkyl, alkenyl, alkoxy or alkenoxy groups.

* * * * *

UNITED STATES PATENT AND TRADEMARK OFFICE
CERTIFICATE OF CORRECTION

PATENT NO. : 5,457,235
DATED : October 10, 1995
INVENTOR(S) : Wand et al.

It is certified that error appears in the above-indentified patent and that said Letters Patent is hereby corrected as shown below:

In column 1, line 8, please rewrite "Pat No. 5,178,79" --Pat No. 5,178,791--

In column 6, line 38, "$R_n-S_iR_c-R_m$" should be rewritten as --$R_n-S_iR_cR_D-R_m$-- and in lines 54 and 55, the spaces should be deleted from the formulas.

In column 9, line 38, --1-- should be inserted after phenol.

Signed and Sealed this

Twenty-seventh Day of February, 1996

Attest:

BRUCE LEHMAN

Attesting Officer        Commissioner of Patents and Trademarks